United States Patent [19]

Stewart et al.

[11] 4,305,278
[45] Dec. 15, 1981

[54] ABRASION TESTING

[75] Inventors: Duncan Stewart; Gwilym I. Williams, both of Slough; David A. Cash, Surrey; Nicholas D. Anstey, Buckinghamshire, all of England

[73] Assignee: Fulmer Research Institute Limited, Buckinghamshire, England

[21] Appl. No.: 128,800

[22] Filed: Mar. 10, 1980

[30] Foreign Application Priority Data

Mar. 21, 1979 [GB] United Kingdom ............... 09953/79

[51] Int. Cl.³ ...................... G01N 15/06; G01N 33/28
[52] U.S. Cl. ...................................... 73/61 R; 73/64; 73/86
[58] Field of Search ........................... 73/86, 7, 64, 61; 324/71 E

[56] References Cited

U.S. PATENT DOCUMENTS 3,124,771 3/1964 Rohrbach ............................... 73/86
4,176,545 12/1979 Oddo ..................................... 73/64

FOREIGN PATENT DOCUMENTS 1557001 1/1969 France ..................................... 73/7
683736 12/1952 United Kingdom .
913490 12/1962 United Kingdom .................... 73/86
1101618 1/1968 United Kingdom .
1138707 1/1969 United Kingdom .
1320736 6/1973 United Kingdom .
1341814 12/1973 United Kingdom .
1402413 8/1975 United Kingdom .
1433315 4/1976 United Kingdom .
1484172 9/1977 United Kingdom .
1499550 2/1978 United Kingdom .

Primary Examiner—S. Clement Swisher
Attorney, Agent, or Firm—Beveridge, Degrandi, Kline & Lunsford

[57] ABSTRACT

Abrasion testing, and hence particle content of fluids including liquids and gases is carried out by abrading a thin film 25 of an electrical conductor with the fluid, and measuring the resulting change in electrical resistance of the film.

The method can be used to monitor metal particles in oil, and hence the state of wear of oil-lubricated metal parts, and the level of particulate pollution in the atmosphere.

16 Claims, 7 Drawing Figures

ABRASION TESTING

The present invention relates to a method for the determination of the degree of abrasiveness of fluid compositions, for example liquids or gases containing particulate matter, such as oils containing metallic particles, and slurries.

A number of methods of sensing wear by measuring the change in electrical conduction of an electrically conductive element are known. For example, British Pat. No. 1,341,814 discloses a device for use in the continuous monitoring of wear at a surface of a machine element, the device including a resistive body and two electrodes attached thereto, the device being situate within the said element, exposed at the wear surface to wear with the element and hence be reduced in current carrying cross-sectional area.

In that prior specification the wearing of the body is caused by a part of the machine with which it is in contact, and not by a fluid. The body is embedded in the element and must be softer than the machine element, so that it does not wear more slowly than the machine element.

Furthermore the resistive body used in this prior proposal is eroded only at its edge so that the sensitivity of the device is slow, significant changes to resistance being achieved only when a large degree of wear to the machine element has take place.

Most commercially available equipment for measuring abrasiveness of slurries is based upon measuring the weight change of a metal test piece which is abraded by the fluid to be tested. The time taken for this wear to occur is often in excess of 1 hour and hence the test cannot be carried out rapidly. The sensitivity of this type of equipment is also low.

The present invention provides a method for determining the degree of abrasiveness of a fluid, for example oil containing low concentrations of metallic particles, or a slurry, which method comprises abrading with the fluid a thin film of an electrically conducting material deposited on the surface of an electrically insulating material and observing the change in electrical resistance of the electrically conducting film.

Measurement of the concentration of metallic particles in oils is of great value in engineering applications, since bearing failure in machinery has been found to be frequently immediately preceded by a sharp increase in metallic particles in the oil with which the bearing is lubricated. The observation of a sudden rise in the quantity of such particles in the oil can prompt detailed examination of the machine, and thus avoid sudden complete breakdown.

The electrically insulating material bearing the conducting film is generally referred to as a testing head, and the testing head may conveniently be formed by depositing the film by means of vacuum evaporation, vacuum sublimation or sputtering.

The invention includes apparatus for determining the abrasiveness of a fluid, which apparatus comprises a testing head, having a thin film of an electrically conductive material deposited on an electrically insulating material, means for making electrical contact with the film to sense its electrical resistance and means for bringing the fluid into contact with the head to abrade the film.

Although the quantity which is directly measured by the method of the invention is the change in electrical resistance of the conducting film, and hence the degree to which the fluid causes the abrasion of the film, this quantity will be an indirect indication in certain circumstances of other parameters of the fluid, such as the concentration of particles therein. Because a comparative rather than an absolute measurement of such parameters is often all that is required, it is to be understood that the term "determining abrasiveness" as used herein includes comparative determinations, and includes determination in any appropriate units (for example in parts by weight equivalent in comparison with a standard).

For convenience, the results shown in the following Examples are shown as a percentage change in resistance $(\Delta R/R) \times 100\%$.

It should also be appreciated that the change in electrical resistance of the film need not be observed directly, since it may be included within a circuit with other compounds, the resistance of which also changes. It is sufficient for the purposes of the invention if any electrical quantity is observed which is responsive to the change in resistance of the film due to wear.

By the term "electrically insulating material" as used herein is meant that the resistance of the said material is not sufficiently low as to render changes in resistance of the film due to abrasion immeasurable, because of bridging by the said material. A material of high resistance is preferred, such as a ceramic insulating material (e.g. alumina, glass, sapphire or porcelain). In the case of alumina the composition can vary from 80% to 100% by weight of $Al_2O_3$. The important features in obtaining consistent measurements are the surface finish and the degree of cleanliness of the head specifically before deposition of the film. The surfaces are therefore preferably fine ground to a surface finish of approximately 25 micro in. (635 nanometers) more preferably of less than 20 micro in. (508 nanometers) and most preferably of less than 15 micro in. (381 nanometers) before the film is applied.

The electrically conducting material is preferably a metal or metal alloy and in practice it has been found that nichrome, having a composition of 80% nickel and 20% chromium is quite suitable. The electrically conducting film is preferably produced by vapour deposition, for example, by vacuum evaporation, vacuum sublimation, or sputtering. The preferred nichrome film is preferably deposited by sublimation from a heated wire in a vacuum chamber, this technique being preferred because it involves relatively low temperatures and helps to maintain a constant alloy composition during deposition. The abrasion of the film with the fluid can cause a significant rise in temperature, and it is therefore desirable that the temperature coefficient of resistance (TCR) of the film material should be as low as possible, in the interests of obtaining accurate and reproducible results. By depositing a film of nickel chromium alloy under a small partial pressure of oxygen (e.g. $10^{-5}$ torr), rather than in vacuo, it is possible to produce films with a very low, and in some cases even a negative TCR. A negative TCR may in favourable circumstances be adjusted to the desired value of approximately zero by heat treatment.

The thickness of the film is preferably 3000 Å (300 n.m.) or less, the most preferred range being from 700 (70 n.m.) to 1000 Å (100 n.m.).

Since in practice it may not be possible to achieve a film with a near zero TCR it is desirable that some means should be provided for allowing for resistance changes consequent to changes in the temperature of the film. This can be done by providing a thermo-couple or similar device in the vicinity of the film. A preferred method of temperature compensation is to provide one or more "control" films on the head, positioned so as not to be abraded, and electrically balanced against the film which is abraded in a resistance bridge circuit.

Changes in the electrical resistance of the film, usually in the range of from 0.001 to 50 ohms, may be determined using circuits for making continuous or intermittent measurements, for example using a bridge circuit. Electrical connections are made between the film and the resistance-measuring circuit.

When a bridge circuit and compensating film is used as outlined above, it is preferred that all four "limbs" of the bridge should be constituted by thin films positioned close to the film which is abraded, although in some circumstances ample accuracy will result if only that limb against which the abraded film is balanced is so positioned. Any such "control" films should desirably be positioned as close to the abraded film as possible, so that its temperature approximates as closely as possible that of the film which is abraded.

It is desirable that the film which is abraded by the fluid should have a resistance which is substantially less than (for example 1/100th of) the balancing resistances in the bridge circuit, in order that gross changes in current flow are minimised when the film is abraded.

Electrical connection with the thin film or films provided on the testing head is preferably effected by means of electrodes (e.g. of gold) deposited on the electrically conducting material in contact with the film or films. In any event, electrical connection will usually be made via a metal dissimilar to the material of the films, and this can result in the production of thermal e.m.f's at the junctions. In order to minimise or eliminate the effect of such thermal e.m.f's, an A.C. bridge circuit (which may be of conventional form) may be employed.

For maximum sensitivity, it is preferred that the film should be abraded over substantially the whole of the width of its resistive area.

A preferred method of carrying out the invention when the fluid has the consistency of a slurry is to pass a substrate coated with the slurry over the surface of the testing head. The substrate may be, for example, Mylar (Registered Trade Mark), or other similar material, and the coating may be applied thereto for example by spraying, dipping or by using conventional coating techniques. It is convenient if the substrate is in the form of a tape, for example a plastic tape, since it may then very readily be kept at a constant tension by means of tensioning arms and spools in a similar manner to those used in commercial tape transport systems for magnetic recording. When this method is used, it is convenient for the testing head to be in the form of a cylinder.

An alternative method of carrying out the invention is to abrade the film directly by means of a high pressure jet of the fluid. This method is particularly suitable for measurements on fluids containing relatively low concentrations of particles, such as oils containing from one to a few thousand parts per million of small metal particles.

The jet is usually arranged so as to strike the film from a distance of a few millimeters, and it has been found that delivery pressures of from 20 to 200 p.s.i. $(1.38 \times 10^5$ to $13.8 \times 10^5$ N/m$^2$) preferably from 70 to 100 p.s.i. $(4.8 \times 10^5$ to $6.9 \times 10^5$ N/m$^2$) give good results using a nozzle approximately 2 mm in diameter.

The nozzle and head may be mounted in a casing to form a cell and the film may be abraded in an atmosphere of air, or the casing may be maintained full of the fluid, in order to minimise the effect of non-uniform abrasion of the film caused by entrained air. An inlet may be provided for maintaining the casing full of the fluid, as well as an outlet for the fluid. Such a cell may be conveniently located in one of the normal oil circulation lines of an oil-lubricated machine, such as an internal combustion engine, so as to be capable of providing continuous monitoring of the state of wear of the machine.

As mentioned above, the method of the invention may be used to monitor the state of wear of one or more oil-lubricated metal bearings, for example in a machine, by continuously or intermittently monitoring the degree of abrasiveness of the oil by the aforesaid method. To this end, the oil may be periodically sampled, and the determination be carried out on separate apparatus according to the invention, or the bearing or machine may be provided with apparatus according to the invention to continuously or intermittently monitor the oil on an "in-line" basis. It is thus contemplated that an aircraft or ship, or each engine of an aircraft or ship, may be provided with apparatus according to the invention, to enable continuous monitoring.

Whatever the arrangement, a sudden rise in the resistance of the film indicates that close examination is necessary to determine whether replacement of metallic parts is required.

The present invention will be further described with reference to the accompanying drawings, in which.

Figure 1:
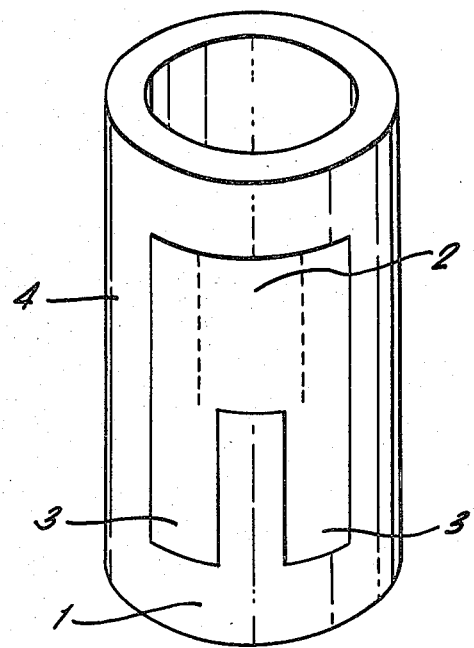
FIG. 1 is a plan view of a wear testing head, used in the method of the invention.

The wear testing head shown in FIG. 1 is particularly suited for use in the method in which the film is abraded by passing a substrate coated with the fluid over the film.

The wear testing head 4 comprises a hollow alumina cylinder 1. Before deposition of the film 2, 3 the external surface of the cylinder is fine ground to a finish of approximately 25 micro in. (365 n.m.) or less. The film is formed so as to define a wear area 2 (i.e. the eventual area of contact between the film and the substrate coated with the slurry containing abrasive particles.

Two electrodes 3 are connected to a suitable bridge circuit (not shown) for measuring the change of resistance of wear area 2.

Figure 2:
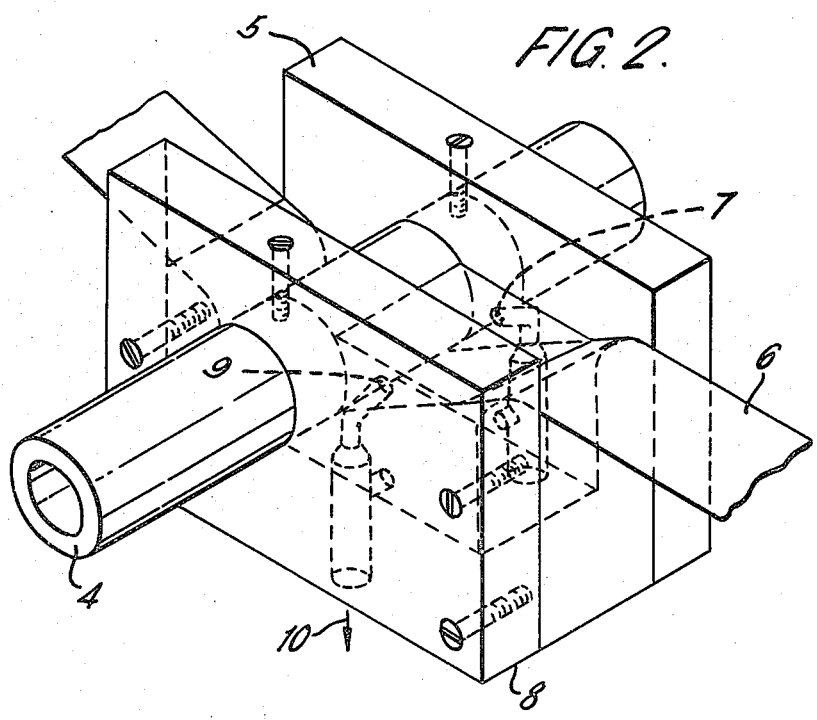
FIG. 2 is a schematic diagram of an abrasion testing unit for use in the method of the invention.

In the abrasion testing unit shown schematically in FIG. 2, the wear testing head 4 is mounted in a block 5. A tape 6 of a substrate material such as Mylar is caused to traverse the wear area of the wear testing head 4. The abrasive slurry is sprayed onto the tape before its passage across the wear area from a pipe 7 which is connected to a slurry inlet 8. Excess slurry is removed from the tape before its passage across the wear area by means of a pipe 9 which is connected to a slurry outlet 10. The tape 6 is caused to traverse the wear area by means of a conventional tape transport system (not shown).

Figure 3:
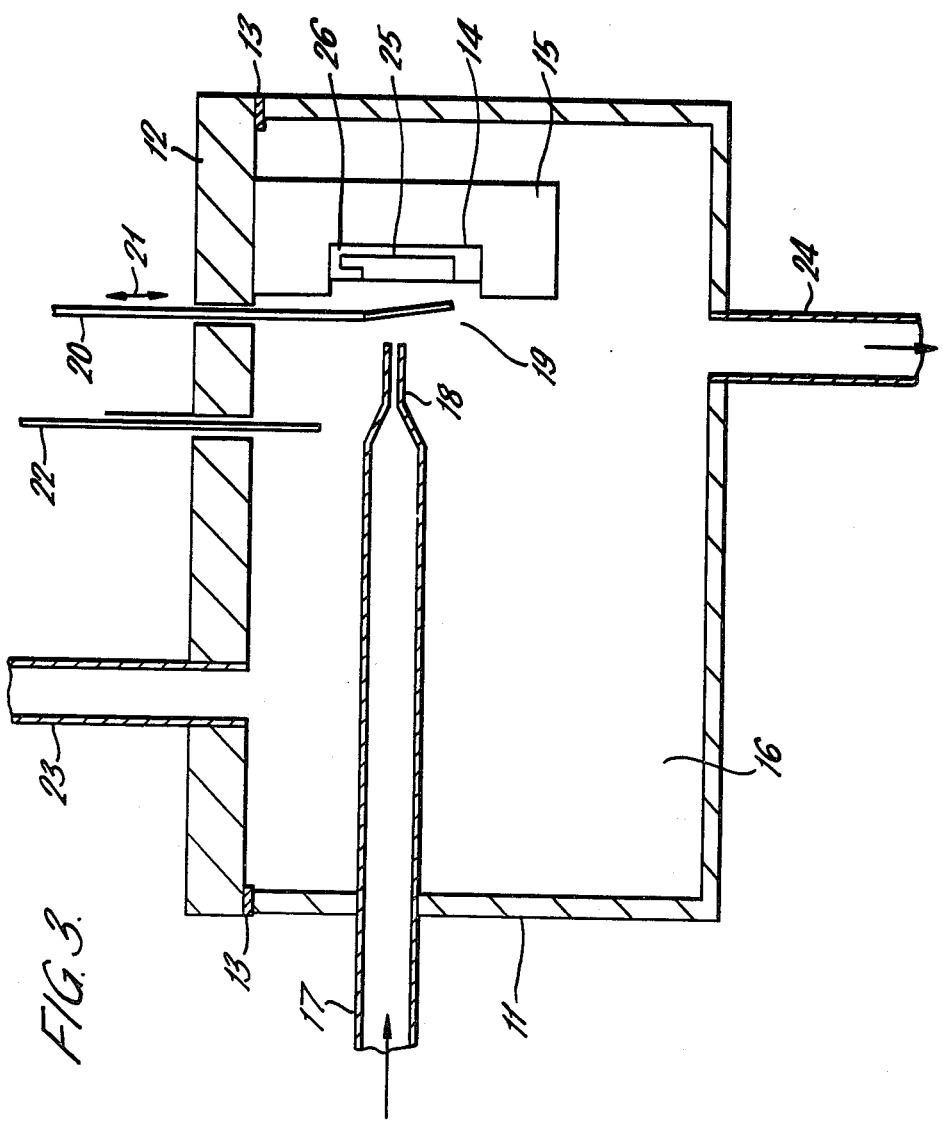
FIG. 3 is a section through an alternative embodiment of an abrasion testing unit.

FIG. 3 shows a section through an abrasion testing unit according to the invention particularly adapted for the measurement of low concentration of metal particles in oils. The unit comprises a steel casing 11 having a Perspex (Registered Trade Mark) top 12 sealed thereto by oil seals 13 to define a chamber 16. A testing head 14 is mounted in a holder 15 positioned at one end of the chamber 16. The head 14 is of the type shown in FIG. 1, although other shapes of head, for example heads in which the film is present on a flat surface, may also be used. The head comprises the abradable film 25, and vacuum deposited gold terminals 26 for making electrical contact therewith.

The electrical resistance of the film 25 is measured by a conventional D.C. bridge circuit (not shown).

An oil supply pipe 17 is arranged so as to direct a jet of oil through the nozzle 18 onto the film of the head 25.

A mask 19 is provided between the nozzle 18 and the head 14, to enable the commencement and termination of the abrasion of the film to be sharp. The mask 19 is secured to a control rod 20, which is slidable in the direction of the arrow 21, so that the mask 19 may be moved between the position shown, in which the film 25 is masked, and a raised position, in which abrasion of the film 25 by the oil is possible.

The temperature within the chamber 16 is sensed by a temperature detector 22, e.g. thermo-couple. The temperature detector 22 is effective mainly when the apparatus is operated full of the fluid (e.g. oil) under test. Fluid inlet and outlet pipes 23 and 24 respectively are provided to facilitate maintenance of the chamber in a fluid filled state.

Figure 7:
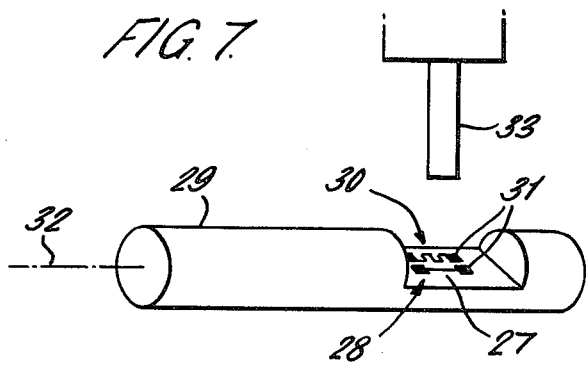
FIG. 7 is a schematic diagram of a further embodiment of apparatus according to the invention.

FIG. 7 is a schematic diagram of apparatus according to the invention in which a nozzle is provided for abrading the film of material.

In FIG. 7, the thin film of nichrome 27 is provided on a flattened area 28 of an alumina rod 29. A compensating film 30 is also provided on the alumina rod. Films 27 and 30 are produced by vapour deposition on the alumina rod using an appropriate mask. Gold terminals 31 are provided at each end of both films, again by vapour deposition using an appropriately formed mask. The electrical resistance of film 30 is approximately ten times that of film 27. Rod 29 is rotatable about its axis 32. In the position shown, a jet of fluid produced by nozzle 33 impinges directly on film 27 at 90°, to abrade the film. It has been found that the optimum angle of incidence for maximum abrasion is approximately 90°.

Abrasion can be terminated by rotating rod 32 about its axis by approximately 180°.

In the resistance measuring circuit (not shown in FIG. 7) film 30 is used as one limb of an A.C. resistance bridge, of which film 27 also forms a limb. Leads (not shown) are used to connect the bridge to film areas 31.

The present invention will be further described with reference to the following Examples.

EXAMPLE 1

A head as shown in FIG. 1 was prepared by applying a nichrome coating approximately 2000 Å (200 n.m.) thick to an alumina cylinder 0.4" (10 m.m.) in diameter by a vacuum deposition technique. The initial resistance between the electrodes 3 was approximately 80 ohms. The head was mounted in a unit as shown in FIG. 2, and used to measure the abrasiveness of slurries containing 10% by weight of china clay. The slurries were applied to a Mylar tape, which was passed over the head at a rate 15/16 inches (23.8 m.m.) per second.

Three separate tests were carried out using china clay slurries giving abrasiveness measurements of 0.125 g, 0.180 g and 0.640 g respectively, when measured in a "Valley tester" (Trade Mark) machine.

Abrasion of the head at the above-mentioned speed for 1 minute resulted in a resistance increase between the electrodes 3 of 0.37 ohms, 0.56 ohms, and 1.68 ohms, respectively.

EXAMPLE 2

Figure 4:
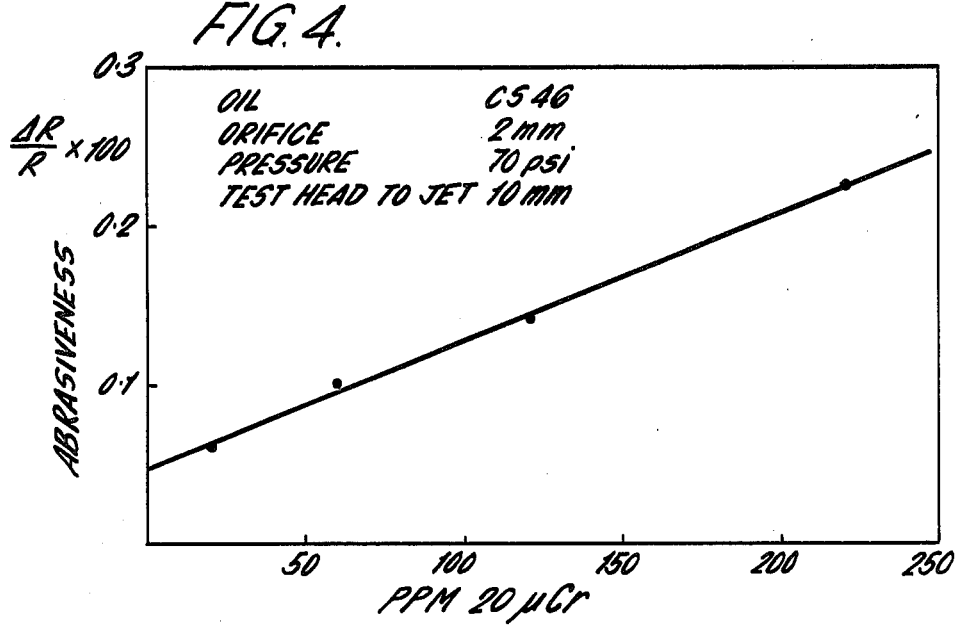
FIGS. 4 to 6 are graphs of results obtained using the unit of FIG. 3.
Figure 5:
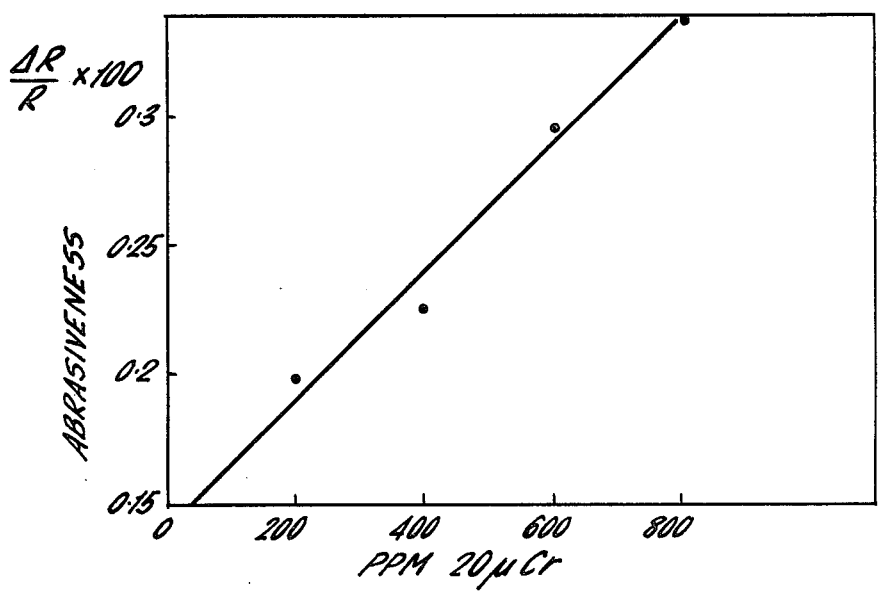

The apparatus shown in FIG. 3 was used to measure the abrasiveness of an oil (British Petroleum Reference No. CS46ISO) doped with varying concentrations of chromium, having an average particle size of 20 $\mu$m. The orifice diameter of the nozzle was 2 m.m. and the distance from the nozzle to the film 10 m.m. The oil was delivered to the nozzle at a pressure of approximately 70 p.s.i. ($4.8 \times 10^5$ N/m$^2$). The results are shown in FIGS. 4 and 5 in terms of the percentage resistance change over a period of approximately 5 minutes.

EXAMPLE 3

Figure 6:
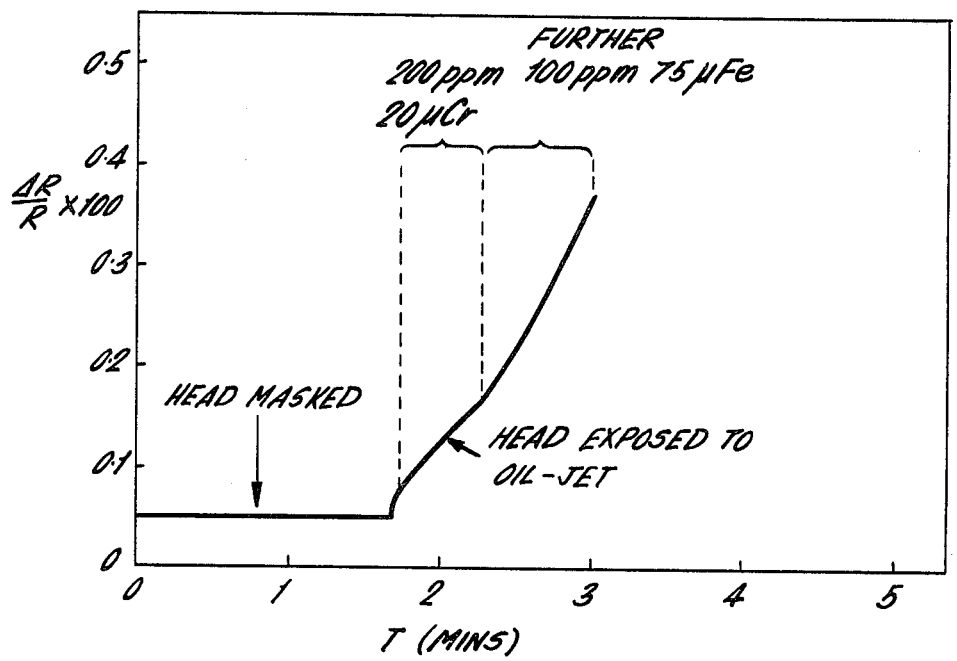

The effect was investigated of abrading the head of the apparatus shown in FIG. 3 with an oil as used in Example 2, and introducing into the oil during the abrasion process a further 100 parts per million of iron particles, having an average diameter of 75 $\mu$m. This illustrates the type of results which might be obtained when the apparatus is used to monitor the state of wear of a bearing, or a machine having a large number of bearings, at bearing failure. The head was initially masked for a period of slightly less than two minutes before abrasion with the oil containing chromium particles, and FIG. 6 shows the trace obtained. A trace of this type would indicate investigation to be necessary, to determine which parts should be replaced to avoid complete breakdown.

Although the operation of the apparatus has been described specifically with reference to liquid-based fluids (i.e. slurries and oils), it is to be understood that the term "fluid" is used herein in its broadest sense, and includes gases. Thus the invention in its broadest sense includes a method of determining the abrasiveness of a gas, and thus indirectly the content of particles in the gas. Such determinations are of increasing value for monitoring atmospheric pollution (for example coal dust) in industrial environments.

Although in the apparatus shown in FIG. 3, the fluid jet strikes the abradable film at an angle of 90°, advantages can be obtained by arranging for the jet to strike the film at an oblique angle, for example at approximately 70°. In certain circumstances this can lead to more consistant abrasion of the film.

We claim:

1. A method for determining the degree of abrasiveness of a fluid, which comprises directing a jet of the fluid at a thin film of an electrically conducting corrosion resistant material on the surface of an electrically insulating material to thereby abrade the film, and observing the change in electrical resistance of the electrically conducting film.

2. A method as claimed in claim 1, wherein the film is a nichrome film.

3. A method as claimed in claim 1, wherein the jet is formed by delivering the fluid to a nozzle at a pressure of from 20 to 200 p.s.i.

4. A method for determining the degree of abrasiveness of a fluid, which comprises passing a substrate coated with the fluid over the surface of a thin film of an electrically conducting material on the surface of an electrically insulating material to thus abrade the film and observing the change in electrical resistance of the electrically conducting film.

5. A method as claimed in claim 1, wherein the film has a thickness of less than 3000 Å.

6. A method as claimed in claim 1, and including the step of sensing the temperature of the film, and compensating for temperature-dependent changes in resistance.

7. A method as claimed in claim 2, wherein the film has a thickness of from 700 to 1000 Å (70 to 100 n.m.).

8. A method as claimed in claim 1 wherein the film has been formed by vapour deposition of the electrically conducting material onto the electrically insulating material.

9. A method of monitoring the state of wear of an oil-lubricated metal bearing, which method comprises determining the abrasiveness of the oil by abrading with the oil a thin film of an electrically conducting material on the surface of an electrically insulating material, and observing the change in electrical resistance of the films.

10. Apparatus for determining the abrasiveness of a fluid, which apparatus comprises a testing head having a thin film of electrically conducting corrosion resistant material deposited on an electrically insulating material, means for making electrical contact with the film to sense its electrical resistance, and a nozzle for directing a jet of the fluid onto the head, to abrade the film.

11. Apparatus as claimed in claim 10, including a mask movable between a first position between the nozzle and the head, and a second position.

12. Apparatus as claimed in claim 10, including a second thin film deposited on or in close proximity to the head, and positioned so as not to be abraded by the fluid, and means for making electrical contact with the second film to sense its electrical resistance.

13. A machine provided with apparatus as claimed in claim 10 adapted for measuring the abrasiveness of oil used in the machine.

14. A method of measuring the particle content of a fluid, which method comprises determining the abrasiveness of the fluid by a method as claimed in claim 1.

15. A method for determining the degree of abrasiveness of a fluid, which comprises abrading with the fluid a thin film of an electrically conducting material which has been vacuum deposited on the surface of an electrically insulating material, and observing the change in electrical resistance of the electrically conducting film.

16. A method for determining the degree of abrasiveness of a fluid, which comprises abrading with the fluid a thin film of an electrically conducting material having a thickness of 3000 Å on the surface of an electrically insulating material, and observing the change in electrical resistance of the electrically conducting film.

* * * * *